United States Patent [19]

Swimm

[11] 3,965,263

[45] June 22, 1976

[54] CHOLINE SALICYLATE COMPOSITIONS AND METHODS FOR ACHIEVING ANALGESIA

[75] Inventor: Walter Thomas Swimm, Darien, Conn.

[73] Assignee: The Purdue Frederick Company, Norwalk, Conn.

[22] Filed: May 12, 1975

[21] Appl. No.: 576,926

Related U.S. Application Data

[62] Division of Ser. No. 401,771, Sept. 28, 1973, Pat. No. 3,898,532, which is a division of Ser. No. 303,920, Nov. 6, 1972, Pat. No. 3,801,613.

[52] U.S. Cl. ............................................... 424/184
[51] Int. Cl.² ........................................ A61K 31/695
[58] Field of Search ...................................... 424/184

[56] References Cited
OTHER PUBLICATIONS

Chem. Abst., vol. 59, 11529a, (1963).

Chem. Abst., vol. 73, 20898j, (1970).

*Primary Examiner*—Stanley J. Friedman
*Attorney, Agent, or Firm*—Wolder & Gross

[57] ABSTRACT

Choline salicylate-silanized silicon dioxide a stable solid, non-hygroscopic composition possessing the full spectrum of analgesic, anti-pyretic and anti-inflammatory properties of choline salicylate is prepared by reaching a choline ion with a salicylate ion and then combining with silanized silicon dioxide in the presence of an inert anhydrous solvent to form the new composition. Solid pharmaceutical dosage forms are prepared with the new composition which are useful in the treatment of musculo-skeletal disease, the relief of pain and the lowering of fever in humans and animals. A method for increasing the concentration of blood salicylate ion through the oral administration of the aforesaid choline salicylate-silanized silicon dioxide and pharmaceutical composition containing the same, is presented.

8 Claims, No Drawings

CHOLINE SALICYLATE COMPOSITIONS AND METHODS FOR ACHIEVING ANALGESIA

This is a division, of application Ser. No. 303,920, filed Nov. 6, 1972, now U.S. Pat. No. 3,801,613, and of application Ser. No. 401,771 filed Sept. 28, 1973, now U.S. Pat. No. 3,898,532.

The present invention relates to solid therapeutic salicylate-containing compositions; a method for their perparation and a method for their use in achieving a therapeutic effect. In particular it is concerned with a solid pharmaceutical compound comprising choline salicylate and silanized silicon dioxide; a method for its preparation, pharmaceutical compositions containing the same, and a method for their use in achieving a therapeutic effect. It is an object of the present invention to describe a solid pharmaceutical composition, choline salicylate-silanized silicon dioxide and capsules, tablets and granules containing the same, which are stable and non-hygroscopic when exposed to the atmosphere for prolonged periods, and which are useful as an analgesic, antipyretic and anti-inflammatory agent.

Choline salicylate is a well defined crystalline compound melting at 49.5°C. to 50.5°C. and has a molecular weight of 241.28. The method for its preparation and its properties are described in U.S. Pat. No. 3,069,321, patented December 18, 1962. A 10 percent aqueous solution of choline salicylate (w/w) has a pH of 6.75 and it does not liberate free salicylate acid above pH 3.5. While choline salicylate is extremely soluble in water, alcohol, acetone and glycerin, it is insoluble in anhydrous ether, benzene and petroleum ether.

Choline salicylate has been established to be a desirable analgesic-antipyretic compound and has noteworthy pharmacologic and therapeutic properties useful in the treatment of a broad range of musculo-skeletal disorders as well as to provide desirable pain relief and antipyresis. Choline salicylate has been shown to possess desirable anti-inflammatory properties and to be useful for administration by oral, rectal, topical and parenteral routes.

Despite its desirable pharmacologic and therapeutic spectrum, choline salicylate has certain inherent limitations in that it is extremely hygroscopic so that the preparation of solid pharmaceutical dosage forms are not readily accomplished. Thus, when crystalline choline salicylate melting at 49.5°C. to 50.5°C. is exposed to even the trace moisture in the atmosphere, it liquifies and after absorption of water, it is virtually impossible to reconstitute into the dry crystalline form. This undesirable hygroscopic property prevents the preparation of solid pharmaceutical dosage forms, as for example, capsules, tablets and granules limiting oral therapeutic usage to essentially liquid dosage forms.

The restriction to liquid oral dosage forms presents well known complications in the handling and dispensing of this important therapeutic agent. Liquid preparations require more expensive packaging and special handling since breakage and spillage on shipment is quite common. Liquid dosage forms do not lend themselves to the need of the traveler or for convenient use by ambulatory, out-patients during the day. Another limitation of the liquid dosage form is the difficulty in achieving a palatable, pleasing taste to mask the inherent characteristic, noxious fishy taste and odor of choline compounds. When such flavoring has been accomplished for certain preparations, it is usually the result of costly developmental research effort, utilizing expensive flavoring agents.

While much research has been expended in attempting to achieve a stable solid non-hygroscopic form of choline salicylate, the results have been generally wanting. Thus, U.S. Pat. No. 3,297,529 (patented Jan. 10, 1967) describes a solid choline salicylate stabilized by the addition of magnesium sulfate to form a non-hygroscopic mixture. The composition described in the aforesaid U.S. Pat. No. 3,297,529 is a solid product varying in composition of from 25 percent to 80 percent choline salicylate and contains from 20 percent to 75 percent of magnesium sulfate. The mixture is described as having varying properties as a function of the ratio of choline salicylate and magnesium sulfate used. Magnesium sulfate is a well known cathartic agent and thereby adds an unwanted cathartic response to the salicylate preparations. It is well known that patients utilizing salicylate therapy for musculo-skeletal disorders require large doses of the salicylate preparation for extended periods of time and in these cases and for these patients the laxative effect resulting from administration of magnesium sulfate would be a serious therapeutic limitation.

Another attempt to avoid the limitation of hygroscopic properties of choline salicylate is found in U.S. Pat. No. 3,326,760, patented June 20, 1967 wherein choline salicylate was found to combine with polygalacturonic acid to result in free-flowing, granular powder which was stable and non-hygroscopic. However, choline salicylate polygalacturonate is a new compound which has a different molecular structure and chemical composition to choline salicylate and therefore may not have the desired scope of therapeutic properties of choline salicylate.

It was unexpectedly found that when choline salicylate is combined with silanized silicon dioxide under anhydrous conditions, that a white granular powder with a faint, sweet odor and a characteristic taste is obtained. The aforesaid choline salicylate-silanized silicon dioxide powder has a pH of 7.7 for a 5 percent (w/w) slurry in water. The new composition is without a sharp melting point, but shows decomposition beginning at 245°C. and is non-hygroscopic, being stable under the usual storage conditions for prolonged periods of time. When exposed to the atmosphere in open plates for a period of 3 months at ambient room temperature, the new composition retains its free-flowing, solid powder characteristics in contrast to crystalline choline salicylate which liquefies in a matter of hours when exposed to the atmosphere.

Silanized silicon dioxide is a hydrophobic substance comprising trimethtlsilyl silicon dioxide in intimate, homogeneous combination and is known in the trade as Silanox, a product distributed by the Cabot Corporation of Boston, Massachusetts. Those versed in the art prefer the term silanized silicon dioxide to describe trimethylsilyl silicon dioxide, although the trade name Silanox is also widely utilized for this compound. Thus, wherever the term silanized silicon dioxide appears in the present description and also wherever the term Silanox is used, these trems may be read interchangeably to mean trimethylsilylsilicon dioxide as representing the same chemical compound. Silanized silicon dioxide, or trimethylsilylsilicon dioxide, or Silanox, is a homogeneous chemical compound with certain chemical composition, having characteristic properties which serve to distinguish and identify this compound.

Silane, a member of the silicon class of chemical compounds, contributes an inherent hydrophobicity and lipophilicity to a silicon dioxide particle, which at the same time has been reduced in particle size to provide an enormous surface area. The basic silicon dioxide particle is produced by the hydrolosis of silicon tetra-chloride in a flame process, to result in a particle that is non-porous and amorphous, and of high purity possessing an enormous specific surface area. The primary particle is about 7 millimicrons in diameter and these particles are concentrated into long-branch micron-size aggregates.

The silicon dioxide particle is normally hydrophilic due to a large number of hydroxyl groups present on its surface and it is this property which is eliminated as a result of the chemical reaction between silicon dioxide and silane, whereby hydrocarbon groups replace many of the hydroxyl groups of the silicon dioxide. Silane is a member of the silicon family containing aliphatic substitution of the hydroxyl group. In the present instance, trimethylsilyl, a silane, is reacted with silicon dioxide to form trimethylsilylsilicon dioxide, or silanized silicon dioxide. The newly formed chemical bond between the silane moiety and silicon dioxide are not responsive to high temperature degradation or solvent extraction. The silanized silicon dioxide particle has been shown to have an amorphous structure by X-ray analysis; a specific gravity of 2.2, and a pH of between pH 8 and pH 10. Laboratory studies have indicated that this compound to be virtually non-toxic when ingested and it does not in general act as a skin-irritant when topically applied.

The new composition, choline salicylate-silanized silicon dioxide is prepared under anhydrous conditions. A preferred method of preparation utilizes equimolar concentrations of choline chloride and sodium salicylate, suspended in acetone which are mixed and refluxed for approximately four hours. After cooling and filtering, silanized silicon dioxide, equivalent in weight to the amount of choline salicylate formed, is added to the filtrate and stirred. An equal volume of petroleum ether is then added and the whole allowed to stand overnight. The solvent is removed and the formed choline salicylate-silanized silicon dioxide is dried at room temperature, under low vacuum, until free of solvent. The resulting formed product is obtained in a better than 90 percent yield and is a stable, solid white granular powder without a definite melting point but showing decomposition at 245°C.

While the preferred ratio of silanized silicon dioxide moiety to choline salicylate moiety is equal parts by weight of silanized silicon dioxide and choline salicylate, an optional range of the ratio of silanized silicon dioxide to choline salicylate is between 30 and 140 parts by weight of silanized silicon dioxide for each 100 parts by weight of choline salicylate. In certain instances and for special purposes a greater or lesser quantity of silanized silicon dioxide for each part of choline salicylate may be used to obtain a solid mass suitable for further pharmaceutical manufacture or even for patient administration as is.

The new formed choline salicylate-silanized silicon dioxide composition possesses all of the pharmacologic and therapeutic properties of choline salicylate and may be used in therapy of humans and animals as a means for increasing the blood level of salicylate ion. Furthermore, it may be utilized with particular advantage whenever salicylate therapy is indicated as an analgesic and antipyretic agent, as well as an anti-inflammatory compound.

After the oral administration of the new composition to humans and animals, there is a rapid systemic absorption of choline salicylate to significantly increase the blood level of salicylate ion. The oral administration of the new composition may be facilitated through pharmaceutically compounding the new stable solid choline salicylate-Silanox into tablets, capsules and granule dosage forms although the choline salicylate-Silanox compound may be administered directly to the human or animal patient.

When a tablet dosage form is desired, then the free-flowing solid powder choline salicylate-Silanox composition is mixed with a suitable binding agent and tablet lubricant and compressed into tablets of desired size and shape. Capsules are prepared by filling appropriate gelatin capsules with a new composition. Granules are prepared by mixing the new composition with a diluent and a granulating agent and passing the mass through a No. 8 U.S. standard mesh sieve and drying the resultant granule. Suitable color and flavoring materials may be added to each of the respective forms, if desired.

The unit dosage concentration of choline salicylate-silanized silicon dioxide utilized to prepare the respective solid pharmaceutical dosage forms will vary according to their intended use.

A preferred concentration of active ingredient in a unit dosage form, as for example, one tablet, one capsule or one teaspoon (3 grams) of granules, is 875 mg. of choline salicylate-silanized silicon dioxide unit dosage form, said formed active ingredient containing equal parts by weight of choline salicylate and silanized silicon dioxide, which concentration is equivalent in salicylate content to the conventional 5 grain aspirin tablet. However, from ¼ to ½ this quantity of active compound may be desired for the preparation of children's tablets, capsules and granules. This dosage may also be desired for geriatric use or for use in the debilitated patient.

For special therapeutic uses, as for example in the treatment of chronic musculo-skeletal disease or in arthritic and rheumatic conditions, the concentration of active ingredient per unit dosage form may be desired to be increased to facilitate the administration of the large quantities of salicylate compound ordinarily utilized. Special tablets and granules containing twice the ordinary unit dose quantity, or 1750 mg. of choline salicylate-silanized silicon dioxide-Silanox compound equivalent to 10 grains of aspirin in salicylate content may be utilized. Granules containing even higher concentration of active ingredient per unit dosage form to be the equivalent of three 5 grain aspirin tablets per unit dose may be prepared with the new composition.

The new composition, choline salicylate-silanized silicon dioxide, is particularly suitable to the preparation of an effervescent dosage form, i.e., granules or tablets. The deliquescent properties and extreme hygroscopicity of choline salicylates has hitherto made it impossible to prepare any effervescent dosage form containing this desirable active ingredient. It is generally accepted than an effervescent salicylate preparation in either the granule or tablet dose form, constitutes a highly desirable therapeutic agent since it combines the gastro-intestinal soothing and buffering properties of the effervescent carrier with the therapeutic properties of the salicylate compound. Such effervescent preparations, to wit, tablets or granules, were hitherto unknown to contain choline salicylate and may be prepared utilizing the new choline salicylate-silanized silicon dioxide-silane compound thereby providing the full spectrum of advantageous properties of choline salicylate with those of the effervescent carrier.

The daily dose of new active compound administered in therapy will generally follow the equivalent salicylate requirements determined for the particular human or animal patient being treated. The daily dosage therefore may range from 875 mg. of active compound per day to as high as 10.5 gm. per day. Generally, the administration of unit dose containing 875 mg. of active compound to a human or animal from one to six times daily, will be sufficient to achieve the desired analgesic, antipyretic and anti-inflammatory action for a majority of patients. It is recognized, however that some human or animal patients will require a greater quantity and others a lesser quantity of active compound per day depending upon the severity of disease present, the general physical status of the patient and the age of said patient.

The following examples illustrate the invention but it is not intended to be limited thereto.

EXAMPLE 1

In a suitable container 261.8 gm. of choline chloride is suspended in four liters of acetone. To this suspension is added 102.2 gm. of sodium salicylate and the whole refluxed for four hours while stirring. The mixture is allowed to cool; the sodium chloride precipitate removed and 454 gms. of trimethylsilyl silicon dioxide (Silanox) is added to the liquid and the whole stirred for one hour, and set aside overnight. The solid formed choline salicylate-Silanox or choline salicylate-silanized silicon dioxide composition is separated from the supernatant solvent and dried under low vacuum. The resultant formed product is a free-flowing white powder obtained in greater than 90 percent yield. The formed product assays to contain between 95 percent and 100 percent of the theoretical quantity of choline moiety and between 100 percent and 101 percent of the theoretical quantity of salicylate moiety. The pH of 5 percent (w/w) in water slurry is pH 7.7. The new composition has a faint, sweet odor and a characteristic taste. It is insoluble in water, alcohol and the common organic solvents. The new compound is stable when stored at room temperature for prolonged periods of time. When exposed to the atmosphere in an open dish for a period of up to three months, it retains its solid, free-flowing, powder characteristics and is not hygroscopic.

EXAMPLE 2

To 241.28 gm. of choline salicylate dissolved in two liters of acetone is added 241.28 gm. of trimethylsilyl silicon dioxide. The mixture is stirred and two liters of anhydrous petroleum ether are added. The whole is set aside for a period of at least 12 hours. The solvent is removed and the residue dried at room temperature to obtain the formed choline salicylate-Silanox composition which corresponds in every way to the product obtained as a result of Example 1 above.

EXAMPLE 3

In a suitable vessel containing three liters of anhydrous ethanol is added one gram molecular weight of choline base and one gram molecular weight of salicylic acid. The mixture is stirred, refluxed for four hours and cooled and 242 gms. of trimethylsilyl silicon dioxide are added and the whole stirred for one hour. Three liters of anhydrous ether are added and the mixture is set aside overnight. The solid precipitate is separated from the solvent and air-dried to obtain the formed choline salicylate-Silanox composition having identical properties as that obtained as a result of Example 1 above.

EXAMPLE 4

In a suitable vessel containing one gram molecular weight of choline bicarbonate in anhydrous isopropanol, is added one gram molecular weight of salicylic acid in small increments. The addition of each increment of salicylic acid is made after the ebullition of carbon dioxide ceases. The mixture is stirred, refluxed for a period of at least one hour; cooled to room temperature and 242 gm. of Silanox is added. One liter of anhydrous chloroform is added and the mixture is set aside for a period of at least 8 hours. The formed precipitate is separated from the supernatant liquid and dried. The resulting formed choline salicylate-Silanox compound is identical to that obtained as a result of Example 1 above.

Equimolar quantities of choline carbonate may be substituted for the choline bicarbonate described above; the remainder of the steps being the same and the resultant product is the same as that obtained as a result of Example 1 above.

EXAMPLE 5

In place of the acetone used as described above, there may be substituted in equal amounts, an anhydrous alcohol of the formula ROH wherein R is an alkyl group of from one to four carbon atoms in chain length.

In place of the petroleum ether utilized in Example 1 above, there may be substituted equivalent amounts of anhydrous ether, benzene, chloroform or mixtures of the same.

In place of the choline chloride utilized as described above, there may be substituted choline bromide, choline iodide, choline sulfate, choline nitrate, choline citrate, choline carbonate, choline bicarbonate, choline formate, choline bisulfate, choline sulfite, choline bisulfite, and choline acetate.

In place of the sodium salicylate utilized as described above, there may be substituted in equal molecular quantities a metallic salicylate salt capable of reacting with said choline salts to form choline salicylate. Such metallic salicylate salts as potassium salicylate, lithium salicylate, calcium salicylate, magnesium salicylate, strontium salicylate, zinc and aluminum salicylate are useful in the above described process. The remainder of the steps being the same and the formed product obtained is identical to that resulting in Example 1 above.

EXAMPLE 6

When it is desired to prepare tablets of the formed new composition choline salicylate-Silanox, then 875 gm. of the new composition obtained as a result of Examples 1 to 5 above, is mixed with diluted absolute alcohol containing a suitable binder such as povidone, starch gelatin, and acacia and passed through a No. 16· U.S. standard mesh screen. The granules are dried, lubricated and compressed into tablets of suitable size and shape so that each tablet contains 875 mg. of the formed choline salicylate-Silanox composition which is equivalent in salicylate content of 5 grains of aspirin. By appropriate adjustment of the concentration of choline salicylate-Silanox composition stable pharmaceutical tablets equivalent to 2.5 grains of aspirin or containing 437.5 mg. of the formed composition per tablet and 1.25 grains of aspirin-equivalent or containing 218.75 mg. of the formed composition per tablet, the tablets are stable and nonhygroscopic when stored for prolonged periods of time.

An alternate procedure to prepare tablets with the formed new composition, trimethylsilylsilicone dioxide-choline salicylate, is to directly compress an appropriate quantity of the active ingredient into tablets of suitable size and shape so that the individual tablets contain a therapeutically sufficient quantity to achieve their desired analgesic, antipyretic or anti-inflammatory effect when administered to a human or animal patient.

EXAMPLE 7

Capsules containing the formed new composition are prepared by filling into appropriate gelatin capsules of suitable size and shape the formed new composition obtained as a result of Example 1 to 5 above so that each capsule contains 875 mg. of the formed new composition when capsules containing an equivalent 5 grains of aspirin are desired, or 437.5 mg. of the formed composition per capsule when capsules, equivalent to 2.5 grains of aspirin are desired, or 218.75 mg. of the formed new composition per capsule when capsules equivalent to 1.25 grains of aspirin are desired. The capsules are stable under the ordinary conditions of storage and are nonhygroscopic.

EXAMPLE 8

Granules are prepared by mixing a suitable quantity of the formed new composition when sufficient quantity of diluent and binders to provide a therapeutically sufficient amount of the formed new active compound in each teaspoonful (3 gm. dose). Thus, when a granule intended to provide a salicylate equivalent of a 5 grain aspirin tablet in each teaspoonful of granules is desired, then 875 mg. of the formed new composition is mixed with 2.13 gm. of diluent, as for an example, starch, dextrose or sucrose and the whole wetted with anhydrous alcohol. The mass is passed through a No. 8 U.S. standard mesh sieve and the granules dried and packaged. By appropriate adjustment of the amount of active material, granules may be prepared to contain the new compound in concentration equivalent of 10 grains of aspirin per unit dose (one teaspoonful of granule) or 1750 mg. of active material per teaspoonful. Granules are stable and non-hygroscopic when stored under the usual storage conditions.

EXAMPLE 9

When it is desired to utilize the new choline salicylate-Silanox compound in therapy then a therapeutically sufficient quantity of the aforesaid compound may be orally administered to a human or animal, or a suitable pharmaceutical dosage form, as for example, a tablet, capsule, or granule, or suspension containing the aforesaid new compound as the active ingredient, is administered by the oral route to a human or animal. While the new compound, per se, or a tablet, capsule or granule containing the new compound is ingested in the solid form, or under certain circumstances, suspended in water to be swallowed directly, the effervescent tablet, and the effervescent powder require prior admixture with water or other suitable fluid (i.e., fruit juices) to permit effervescence, in order to obtain the full beneficial effect of the respective effervescent preparation.

Irrespective of the therapeutic dosage form preferred to administer the active compound, the amount of active compound administered per day to a human or animal will depend upon the nature of the disease being treated and the particular needs of the patient. While it may be sufficient to administer a single dose containing 875 mg. of the formed new active compound to provide analgesic relief to a patient presenting a complaint of simple headache, larger quantities will be required for those patients with the more complex musculo-skeletal disorders, as for example, rheumatic and arthritic disease, and these may range as high as 20 gm. of the new compound per day. Clinicians conducting the well known therapeutic regimens utilizing salicylate-containing medications, will adjust the dosage to the patient's requirements, and generally the medication will be administered by the oral route in divided doses of from one to six times daily. Children, geriatric patients and debilitated patients may require quantities as low as 220 mg. of the active compound per unit dose, whereas those with the more severe pathologic entities may require as much as 1.75 gm. of active compound per unit dose. This concentration of active ingredient pertains to all of the pharmaceutical dosage forms.

When choline salicylate-Silanox compound is administered to a human or animal either in the form of a capsule, tablet, granule, effervescent tablet or effervescent granule, then a prompt and rapid elevation of the blood level of salicylate ion will be observed without coincidental gastrointestinal distress or gastric bleeding as is commonly known to occur after the administration of the conventional salicylate compound, i.e., sodium salicylate and aspirin.

What is claimed is:

1. The method of achieving analgesia in an animal or a human comprising administering to said animal or human a therapeutically sufficient quantity of choline salicylate trimethylsilylsilicon dioxide.

2. The method of achieving analgesia in an animal or human comprising administering to said animal or human a therapeutically sufficient quantity of choline salicylate trimethylsilylsilicon dioxide in tablet dosage form.

3. The method of achieving analgesia in an animal or a human comprising administering to said animal or human a therapeutically sufficient quantity of choline salicylate trimethylsilylsilicon dioxide in capsule dosage form.

4. The method of achieving analgesia in an animal or human comprising administering to said animal or human a therapeutically sufficient quantity of choline salicylate trimethylsilylsilicon dioxide in granule dosage form, said granules having a particle size of between 8 and 20 U.S. standard mesh screen size.

5. A solid pharmaceutical composition for administering a salicylate-containing compound to an animal or human comprising an amount of 218 mg. to 875 mg. of choline salicylate trimethylsilylsilicon-dioxide and a pharmaceutically acceptable carrier therefor.

6. A solid pharmaceutical composition for administering a salicylate-containing compound to an animal or human comprising an amount of choline salicylate trimethylsilylsilicon-dioxide sufficient to provide 250 mg. of salicylate moiety and the whole being compounded into a tablet.

7. A solid pharmaceutical composition for administering a salicylate-containing compound to an animal or human comprising an amount of choline salicylate trimethylsilylsilicon-dioxide sufficient to provide 250 mg. of salicylate moiety and the whole being compounded into a capsule.

8. A solid pharmaceutical composition for administering a salicylate-containing compound to an animal or human comprising an amount of choline salicylate trimethylsilylsilicon-dioxide sufficient to provide 250 mg. of salicylate moiety in each 3 gms. of said solid pharmaceutical composition and the whole being compounded into granules having a particle size of between 8 and 20 U.S. standard mesh screen size.

* * * * *